(12) United States Patent
Gamache et al.

(10) Patent No.: US 7,028,563 B2
(45) Date of Patent: Apr. 18, 2006

(54) FLUID SAMPLING SYSTEM AND METHOD THEREOF

(75) Inventors: Yves Gamache, Adstock (CA); André Fortier, Adstock (CA)

(73) Assignee: Systeme Analytique Inc., Quebec (CA)

( * ) Notice: Subject to any disclaimer, the term of this patent is extended or adjusted under 35 U.S.C. 154(b) by 166 days.

(21) Appl. No.: 10/818,771

(22) Filed: Apr. 5, 2004

(65) Prior Publication Data

US 2005/0217391 A1 Oct. 6, 2005

(51) Int. Cl.
*G01N 1/00* (2006.01)
(52) U.S. Cl. .................................................. 73/863.33
(58) Field of Classification Search ................. 73/1.01, 73/863, 863.31, 863.33, 863.81, 864.73, 73/864.81, 23.42; 137/861, 862, 870
See application file for complete search history.

(56) References Cited

U.S. PATENT DOCUMENTS

| | | | |
|---|---|---|---|
| 3,069,898 A * | 12/1962 | Vesper | 73/23.42 |
| 3,426,599 A * | 2/1969 | Sternberg et al. | 73/864.81 |
| 3,800,593 A * | 4/1974 | Bradley | 73/864.81 |
| 5,054,309 A | 10/1991 | Mettes et al. | |
| 5,055,260 A | 10/1991 | Roberge et al. | |
| 5,065,794 A | 11/1991 | Cheung | |
| 5,239,856 A | 8/1993 | Mettes et al. | |
| 5,259,233 A | 11/1993 | Brandt | |
| 5,447,053 A | 9/1995 | Ohmi | |
| 5,469,751 A * | 11/1995 | Weiss et al. | 73/863.33 |
| 5,587,519 A | 12/1996 | Ronge et al. | |
| 5,661,225 A | 8/1997 | Ridgeway et al. | |
| 5,922,286 A | 7/1999 | Girard et al. | |
| 6,637,277 B1 | 10/2003 | Gamache et al. | |

OTHER PUBLICATIONS

Jean-Marc Girard and Yves Marot, "PPT Level Analysis of UHP Hydrogen", European Semiconductor, 1996.

* cited by examiner

*Primary Examiner*—Robert Raevis
(74) *Attorney, Agent, or Firm*—Darby & Darby

(57) ABSTRACT

A fluid sampling system and a method thereof are provided. The fluid sampling system is provided with a plurality of sampling channels, each of the sampling channels comprising a sampling line having an inlet, a regulated outlet, and first and second calibrated flow orifices connected in series between the inlet and outlet. Each of the sampling channels also comprises a controllable derivation line connected between the first and second orifices, for deviating fluid from the sampling line. The fluid sampling system is also provided with a connecting line for connecting together the outlets of the sampling lines. The connecting line has a main regulated outlet for providing a fluid sample. The fluid sampling system also comprises control means for controlling pressures between first and second orifices of all of the sampling lines by means of the controllable derivation lines, thereby increasing pressure between first and second orifices of one of the sampling lines which is then selected to provide the fluid sample to the outlet of the connecting line, and decreasing pressure between first and second orifices of remaining sampling lines to back purge the remaining sampling lines. Such a fluid sampling system does not contaminate the sample by the product that is out gassed or adsorbed by the control means used to control fluid flows.

17 Claims, 9 Drawing Sheets

FLUID SAMPLING SYSTEM AND METHOD THEREOF

FIELD OF THE INVENTION

The present invention generally relates to the field of fluid sampling and concerns more particularly a fluid sampling system and a fluid sampling method particularly adapted for use in a gas analysis process.

BACKGROUND OF THE INVENTION

In all fields using a gas medium or a liquid medium such as air separation processes, petroleum refining, natural gas production, semiconductor devices manufacturing, specialty gas laboratories, etc . . . , all gas being processed or used in one way or another must be analyzed for quality control or process control. To perform such an analysis, a gas sample is collected and brought to an analytical measuring system. Generally, the gas sample is conveyed through metal tubing, up to a sample panel. A plurality of samples may need to be successively collected, depending on the complexity of a particular system. The analyzed sample should of course be representative of the gas medium being controlled.

The industry has used and still uses various devices and processes to bring a sample to an analytical system. With these sampling systems, contamination of a sample often occurs by mixing it with previously selected samples, leaks in or out of the sampling system or leaky valves.

Another unavoidable source of contamination are the control elements, i.e. valve, mass flow controller, pressure regulator, etc . . . , used to select and control flow of various sample streams. In U.S. Pat. No. 5,922,286 and in "Ppt level analysis of UHP Hydrogen", European Semiconductor, 1996, it has been shown that any on-line component such as valve, mass flow controller, etc . . . , will act as a quasi continuous source of contamination when attempting to measure very low levels of impurities, i.e. ppb (part per billion) and ppt (part per trillion) level. These components will outgas some different types of molecules based on material used to manufacture them. When measuring particle contamination for process gas in semi-conductor industries, often, the limit of detection is limited by various types of control elements. Sudden change in flow and pressure generates wide variation in readings. For particle measurement, constant pressure flow is required. As indicated in the above mentioned U.S. Pat. No. 5,922,286 and as well known by people involved in the art, transient pressure or flow rate change system equilibrium, leading thus to an adsorption or desorption phenomenon. This lead to long purging time to recover system equilibrium.

Presently used in the art, there is a system provided with various sample lines made of various tubing material, each bringing a corresponding sample to an apparatus sample inlet. A plurality of sampling locations may be provided, as required by the process to be monitored. A bypass rotometer is provided in each line for purging a given sampling line when not selected. The rotometer allows fixing of a bypass flow and preferably sets a high flow in the sample line to speed up the purge time. The excess flow is vented out of the system. A female quick connector is provided at the extremity of each sampling line and is adapted to receive a male quick connector allowing the sample to flow through a flexible line up to the analytical system. To change the selected sample line, the male quick connector needs to be removed from the female quick connector and inserted in another one. This system makes sure that there is no sample cross contamination from various sample points, since the sampling lines are physically isolated. However, this system has serious drawbacks. First, each time the male quick connector is disconnected from a female quick connector, the gas flow to the analytical system is momentarily interrupted. Some analytical systems are affected by the sample flow variation. Also the female and male quick connectors have some internal dead volume that will be filled with atmospheric air when disconnected from each other. This air is directed to the analytical system and serious pollution may occur when measuring $H_2O$, $O_2$ or $N_2$ as impurities in a particular background. Another drawback is that the quick connectors tend to wear out with use, resulting in leaks leading to wrong analytical results. Another problem with this system is related to the use of flexible tubing. Often this tube is made of various plastic or polymers that exhibit too much permeation to $O_2$ and $H_2O$, thereby polluting the sample. When flexible metal tubing is used, it must be replaced often since metal fatigue due to manipulation causes them to break. Another drawback is that such quick connectors have a o-ring that is used to seal them. The material used to make these o-rings will adsorb or desorb some of the impurities to be measured, so it changes the sample composition, making them a poor choice for low-level measurement.

Also used in the industry, there is another sample stream selection system quite similar to the one just described above. This second system uses, instead of quick connectors, a rotary selection valve well known in the industry and available from various manufacturers. This system alleviates some of the drawbacks of the previous one, but introduces cross port flow contamination that increases with time. If a sample line has a higher pressure, it will leak through a valve body and pollute the stream being measured. This valve requires frequent replacement. Furthermore, leaks can occur from the valve stem.

Also known in the art is another system wherein each sampling line includes an ON/OFF valve provided downstream a bypass rotometer. However, this system introduces dead volume in the line section downstream the valve. When switching from one sample to a new one, the line section of the previously selected sample is full of the previous sample. This gas is trapped there and will slowly diffuse in the line, slowing down the response time of the system and causing drifting readings of the analytical system. Another source of unswept dead volume is the valve itself. The space surrounding the valves plunger is always filled with sample gas and slowly diffuses in the main stream, causing measurement drift and noise. A Diaphragm based valve may be used to reduce the problem, but it increases the cost of the system since most of the time the use of such a valve will involve orbital welding for assembly. Furthermore, over time, ON/OFF valves will develop leaks. So an unselected stream may leak to a selected one, resulting in analytical error measurement and apparent drift or noise when the sample line pressure varies again. As soon as a valve develops a leak it must be replaced, interrupting the system in service. There are some variations of the previously described systems but all have similar drawbacks.

Also known in the art is the above mentioned U.S. Pat. No. 5,922,286 (Girard et al). Girard discloses a system that selects individual sample streams with the help of a 4-way, pneumatic actuated, VCR ¼" connected diaphragm valve. Even if this system succeeds in eliminating unswept volume present on the discharge side of the valve and provides some means to have a sample inlet bypass flow or purge, it fails to eliminate the problem associated with leaking valves, i.e.

crossport flow contamination. The selected sample must flow through all unselected valve bodies just around the seat, which is quite large. Therefore, the risk of crossport contamination increases with the number of sampling lines in the system. Diaphragms having a relatively short useful life, there will eventually be leaking across the seat and contamination of the selected sample will occur. Finally the diaphragm valves used in this system are costly and the total space required for this system is quite large.

Also known in the art is U.S. Pat. No. 6,637,277 by the same inventor of the present invention. In this patent, Gamache discloses a system that eliminates problems related to dead volume and leaking in valves by adding back purge flow on the discharge side of the valves, as illustrated in FIG. 1. Even if this proposed system corrects the inherent problems of all other previously described systems, the control valve (on-off valve) is still in contact with the process fluid to be analyzed, then contaminating it.

Other related prior art systems include U.S. Pat. Nos. 5,054,309; 5,055,260; 5,065,794; 5,239,856; 5,259,233; 5,447,053; 5,587,519 and 5,661,225.

In all prior art referred here, the sample to be introduced in the high sensitivity analytical system passes through the control element in some way. So, in all these cases the sample may be affected in some manner that leads to modify its level of impurities, leading to erroneous measurement.

SUMMARY OF THE INVENTION

It is an object of the present invention to provide a fluid sampling system that prevents cross-port flow contamination between various sampling lines and that does not contaminate the sample by the product that is out gassed or adsorbed by the control element used to control flow of process fluid.

Accordingly, the present invention provides a fluid sampling system including a plurality of sampling channels. Each of the sampling channels is provided with a sampling line having an inlet, a regulated outlet, and first and second calibrated flow orifices connected in series between the inlet and outlet. Each of the sampling channels is also provided with a controllable derivation line connected between the first and second orifices, for deviating fluid from the sampling line. The fluid sampling system also comprises a connecting line for connecting together the outlets of the sampling lines. The connecting line has a main regulated outlet for providing a fluid sample. The fluid sampling system is also provided with control means for controlling pressures between first and second orifices of all of the sampling lines by means of the controllable derivation lines, thereby increasing pressure between first and second orifices of one of the channels which is then selected to provide the sample fluid to the outlet of the connecting line, and decreasing pressure between first and second orifices of remaining sampling lines to back purge the remaining sampling lines.

According to another aspect of the present invention, there is also provided a fluid sampling method comprising the steps of:

a) providing a plurality of sampling channels, each of the sampling channels comprising a sampling line having an inlet, a regulated outlet, and first and second calibrated flow orifices connected in series between the inlet and outlet;

b) connecting together the outlets of the sampling lines to provide a main regulated outlet;

c) providing fluids to the inlets of the sampling lines;

d) deviating in a regulated manner the fluids from points located between the first and second flow orifices of the sampling lines; and e) after the steps a), b), c) and d), increasing pressure between first and second orifices of one of the sampling lines which is then selected to provide a fluid sample at the main outlet, and decreasing pressure between first and second orifices of remaining sampling lines to back purge the remaining sampling lines.

BRIEF DESCRIPTION OF THE DRAWINGS

These and other objects and advantages of the invention will become apparent upon reading the detailed description and upon referring to the drawings in which.

Figure 1:
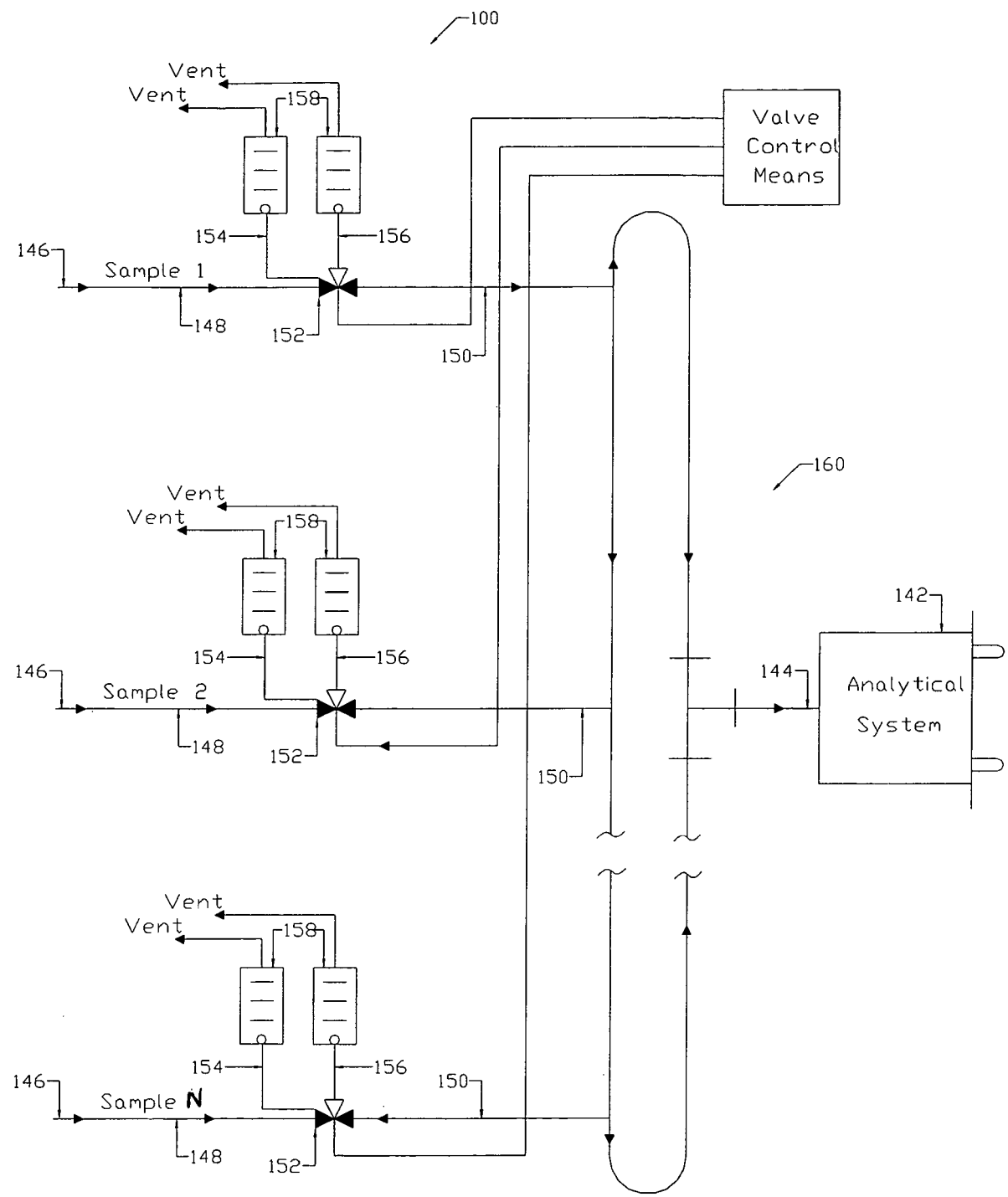
FIG. 1 (prior art) is a schematic representation of a fluid sampling system known in the art.

While the invention will be described in conjunction with example embodiments, it will be understood that it is not intended to limit the scope of the invention to such embodiments. On the contrary, it is intended to cover all alternatives, modifications and equivalents as may be included as defined by the appended claims.

DETAILED DESCRIPTION OF THE FIGURES

In the following description, similar features in the drawings have been given similar reference numerals and in order to weight down the figures, some elements are not referred to in some figures if they were already identified in a precedent figure.

Referring to FIG. 1 (prior art), there is shown a fluid sampling system 100 for providing a fluid to a fluid processing apparatus 142 presently used in the art. The system 100 includes a plurality of sampling channels 146, each having an inlet line 148 and an outlet line 150 connected by a valve 152. The valve 152 has a closed position preventing a fluid flow between the two lines 148, 150 and an opened position allowing such a fluid flow. A first and a second purge line 154, 156 are provided, respectively connected to the inlet and outlet lines 148, 150 for purging fluid therefrom. Rotometers 158 or other similar devices are provided for controlling each of the purge lines 154, 156. A connecting line 160 is provided for connecting each of the outlet lines 150 to each other and to the outlet 144. In operation, one of the valves 152 is opened and the others are closed. Fluid flows from the selected valve to the apparatus 142 and backwards through the outlet lines 150 of the unselected sampling channels 146, providing a backpurge of these outlet lines through the second purge lines 156. In this system 100, the valves 152 are in contact with the process fluid to be analyzed and this can therefore lead to a contamination of the sample to be analyzed.

Figure 2:
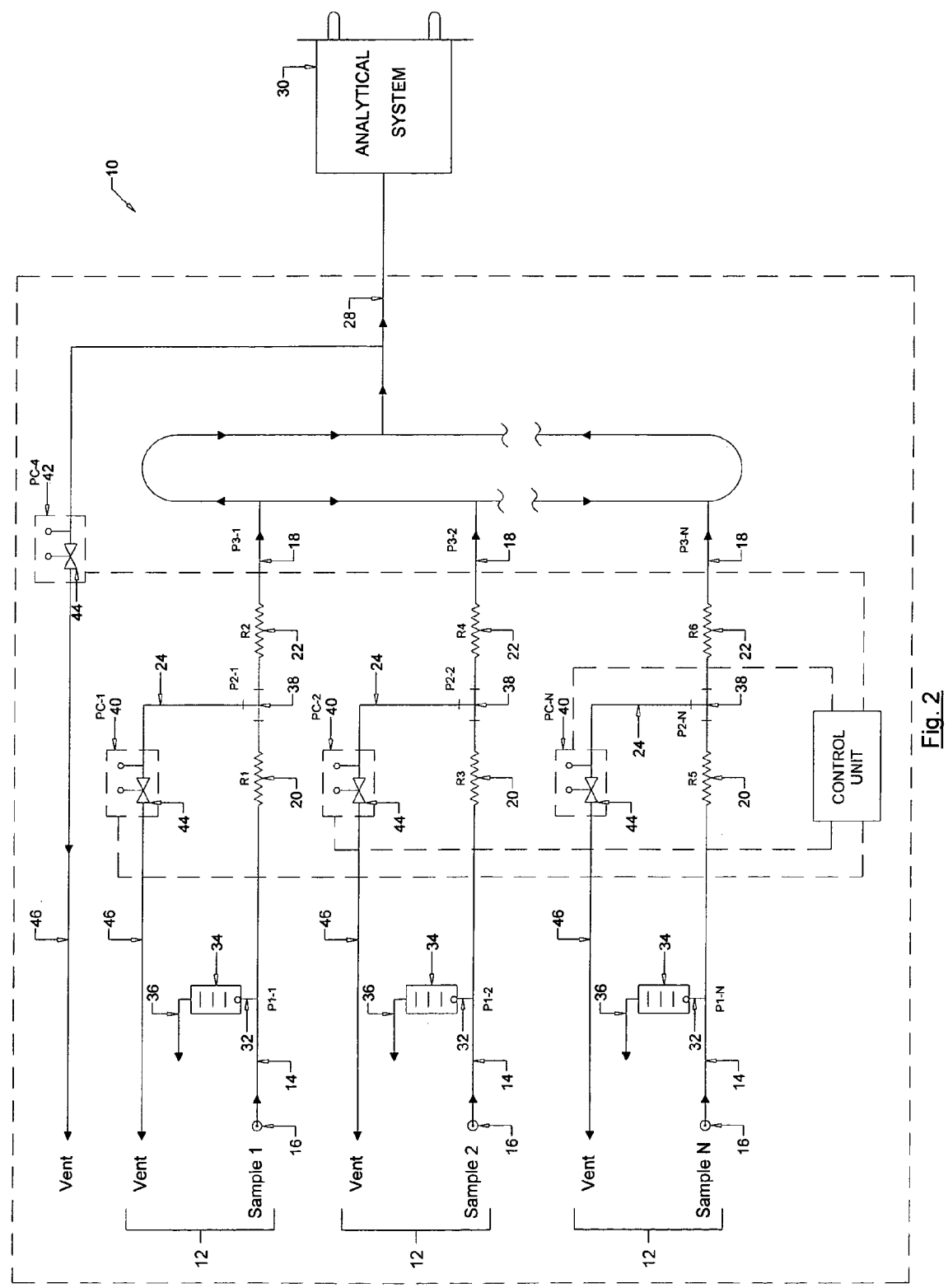
FIG. 2 is a schematic representation of a fluid sampling system according to a preferred embodiment of the present invention.

Referring to FIG. 2, there is shown a fluid sampling system 10 according to a preferred embodiment of the present invention. Contrary to the prior art system 100 just described above with reference to FIG. 1, the fluid sampling system 10 of the present invention does not contaminate the sample to be analyzed. The fluid sampling system 10 provides a fluid sample to at least one fluid processing apparatus here embodied by an analytical system 30. It is however understood that the present system may for example alternatively be used to feed a process using fluid samples, or any other type or number of apparatus adapted to receive a fluid from a given medium. Also, in the illustrated embodiments the fluid sample is of the gaseous type, but the present invention may just as well be used to sample a liquid medium. The fluid sampling system of the present invention that will be described thereinafter can advantageously be inexpensively manufactured.

The fluid sampling system 10 is provided with a plurality of sampling channels 12. Each of the sampling channels 12 is provided with a sampling line 14 having an inlet 16, a regulated outlet 18, and first and second calibrated flow orifices 20, 22 connected in series between the inlet 16 and outlet 18. The sampling lines 14 may come from different sample points in a particular process and therefore, may have different length. Thus, the fluid sampling system 10 may advantageously have regulating means for regulating the inlets 16 of the sampling lines 14. Preferably, the regulating means have a plurality of purge lines 32 respectively connected between the inlet 16 and the first orifice 20 of each of the sampling lines 14. Preferably, each of the purge lines 32 is provided with a purge flow controller 34 connected to a vent line 36. The purge flow controller 34 is preferably mounted with a valve. The purpose of this flow controller 34 is to allow a large sample flow to react rapidly in response to a process change. This can also be useful when the sample point is located far away from the sampling line. Each of the sampling channels 12 is also provided with a controllable derivation line 24 connected between the orifices 20, 22, for deviating fluid from the sampling line 14. Each of the sampling lines 14 may advantageously be provided with a T-type of joint 38 for connecting the corresponding controllable derivation line 24 between the corresponding orifices 20, 22. The fluid sampling system 10 is also provided with a connecting line 26 for connecting together the outlets 18 of the sampling lines 14. The connecting line 26 has a main regulated outlet 28 for providing a fluid sample to the processing apparatus 30. The fluid sampling system 10 is also provided with control means for controlling pressures between orifices 20, 22 of all of the sampling lines 14 by means of the controllable derivation lines 24, thereby increasing pressure between orifices 20, 22 of one of the sampling lines 14 which is then selected to provide the fluid sample to the outlet 28 of the connecting line 26, and decreasing pressure between orifices 20, 22 of remaining sampling lines 14 to back purge the remaining sampling lines 14. In other words, by controlling the pressure at the connecting point located between first and second orifice 20, 22, the fluid of one sampling line 14 is directed to the fluid processing apparatus 30 while the fluids of the remaining sampling lines 14 are vented out through their respective derivation lines 24.

As illustrated in this preferred embodiment, the control means may advantageously comprise a plurality of pressure regulators 40 respectively connected to the derivation lines 24 for regulating pressure therein, thereby controlling the pressures between orifices 20, 22 of the sampling lines 14. Moreover, the control means may advantageously further comprise an outlet pressure regulator 42 connected to the main outlet 28 of the connecting line 26 for regulating pressure therein, thereby controlling an output pressure at the main outlet 28. Preferably, the outlet pressure regulator 42 and each of the pressure regulators 40 comprises a back pressure regulator 44 having a discharge side connected to a vent line 46. Also preferably, the control means further comprise a control unit 54 operatively connected to the outlet pressure regulator 42 and to each of the pressure regulators 40 for controlling the output pressure at the main outlet 28 and the pressures between orifices 20, 22 of all of the sampling lines 14. Also preferably, the connecting line 26 of the fluid sampling system 10 is loop-shaped so that it allows an equal purging time for any of the sampling channels 12.

Still referring to FIG. 2, the following discussion explains in more details how the fluid sampling system 10 can be operated. Let's assume for the sake of discussion that P1-N is the inlet pressure of sampling line N. P2-N is the pressure at the connecting point between orifices 20, 22 and P3-N is the outlet pressure of sampling line N. So P1-1, P2-1, P3-1 are the pressures for channel one and P1-2, P2-2, P3-2 for channel two and so on. Orifices 20, 22 of channel one are respectively R1 and R2, orifices 20, 22 of channel two are respectively R3 and R4, and orifices 20, 22 of channel three are respectively R5 and R6. Let's now assume that one likes to sample channel one. To do so, the following initial condition must be respected: P1>P2>P3 for channel one, while P1>P2<P3 for all other channels. When this condition occurs, the process fluid flows through R1 and R2 and then through the loop-shaped connecting line 26 and the analytical system 30. At the same time, the selected process fluid from sampling channel one flows back in all orifices 22, R4 and R6, of the remaining channels 12 for back purging them and eliminating the undesirable effects of dead volume.

According to a typical application for the measurement of $N_2$, $O_2$, $H_2O$ particles, etc . . . by a gas process analyzer, or for directing a process gas to an APIMS (Atmospheric Pressure Ionization Mass Spectrometer) or Hydrocarbon measurement, the selection of the hardware of the fluid sampling system 10 is determined in view of the characteristics of the application, i.e. sampling line inlet condition required to operate the analytical system 30, the numbers of sampling channels 12, gas type and the minimum vent flow required to avoid atmospheric air back diffusion into the system. Thereinafter, there is described a typical step-by-step procedure to determined the specification of orifices 20, 22 of the fluid sampling system 10.

Typically, the request comes from a customer who needs a high performance analytical system. Most of the time, such system will be used where the level of impurities to be measured are very low, i.e. ppt (part per trillion), ppb (part per billion) or sub ppm (part per million) levels. Such high purity gases are mainly used in the electronic manufacturing industries, but it should be understood that the fluid sampling system 10 of the present invention may also be used in other fields of application. For example, a gas producer will use the system for process control or for quality control of the final product. In such application, the impurities to be measured can be $H_2$, Ar, $O_2$, $N_2$, $CH_4$, CO, $CO_2$ and non methane Hydrocarbons (NMHC) in $H_2$, $O_2$, $N_2$, Ar or He.

Typically the analytical system is a high sensitivity gas chromograph using different types of detectors manufactured by various gas chromograph companies. Typically, such gas chromograph will conveniently perform with a sample inlet pressure of 35 Kpag and a sample flow therein of 75 sccm. These are typical values for many gas analysers but it should be noted that other values could also be conveniently used. Let's also assume that one needs to measure an argon gas background. Based on these data, orifices 20, 22 have to be sized in relation to pressures and flows of this application. It should also be noted that designing a system for argon will also work for other gases of similar viscosity like $O_2$, $N_2$, etc . . . . So, these values given above are the first operating parameters of specifications, but other values could also be conveniently envisaged as well known in the art.

Figure 3:
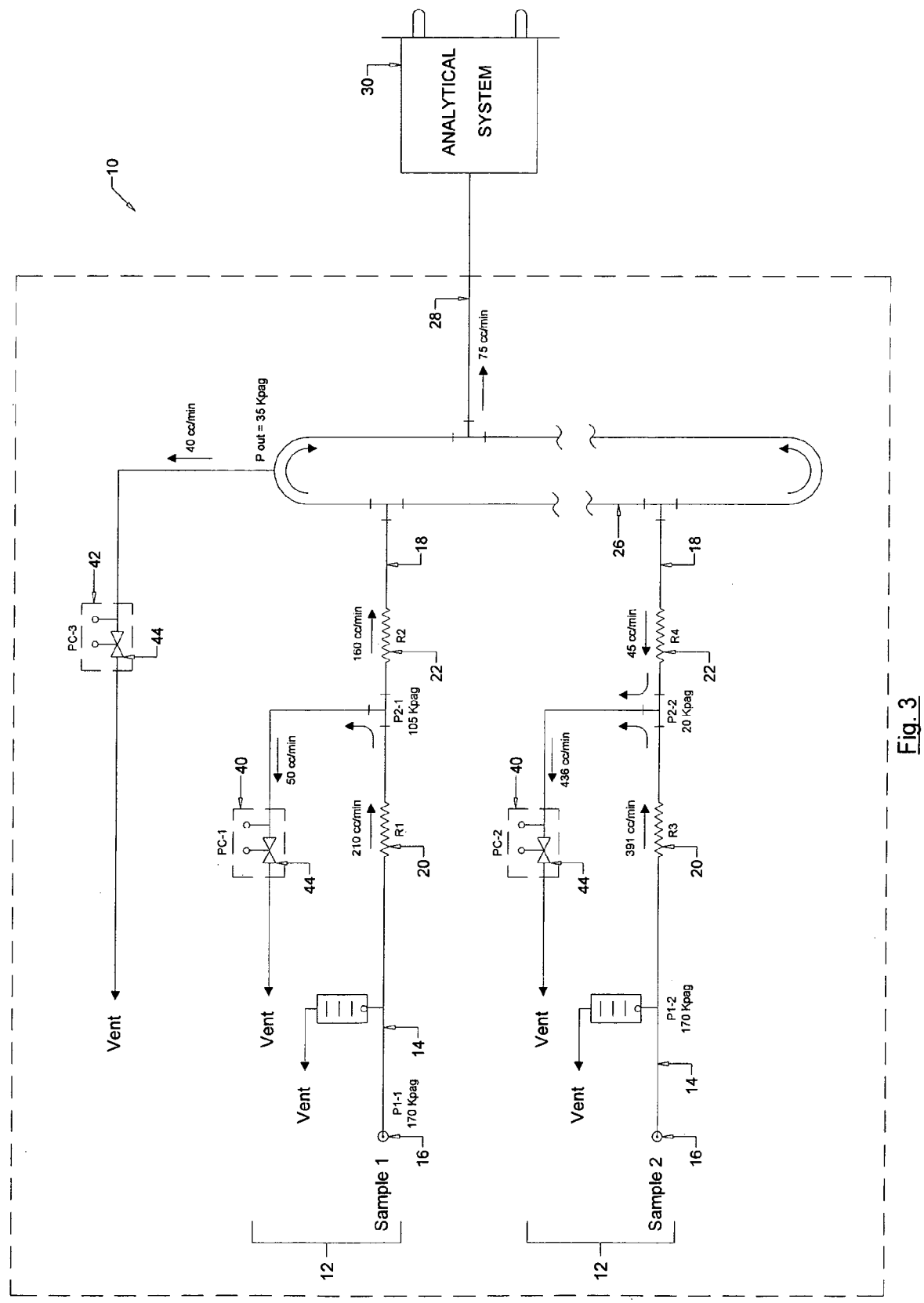
FIG. 3 is a schematic representation of a fluid sampling system according to another preferred embodiment of the present invention, in a first operating position.
Figure 4:
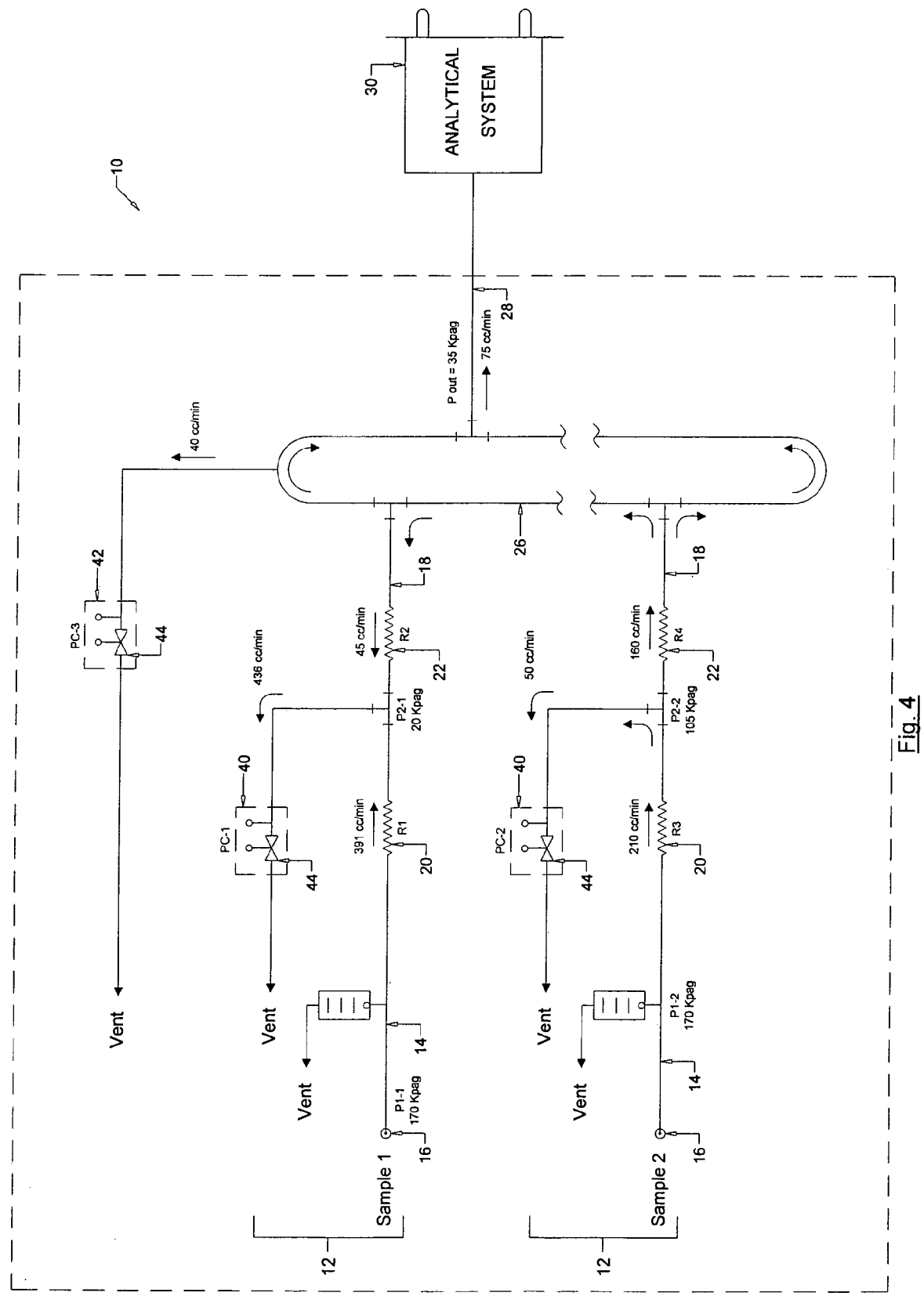
FIG. 4 is a schematic representation of the fluid sampling system of FIG. 3, in a second operating position.

Referring now to FIGS. 3 and 4, there is shown a two-channels fluid sampling system 10 according to another preferred embodiment of the present invention. FIG. 3 shows different fluid directions and pressures when channel one is selected while FIG. 4 shows them when channel two is selected. As already defined, P-out is 35 kpag and inlet flow to the analytical system 30 is 75 sccm. To maintain the output pressure at 35 Kpag, a back pressure regulator 44 is used. Its set point is set at 35 Kpag. The fact of adding this back pressure regulator 44 introduces a dead volume that is between the connecting line 26 and the outlet back pressure regulator 44. So to eliminate the undesirable effect of this dead volume a purge flow has to be performed constantly. It is well known from people involved in the art that a line that vents some gas to atmosphere is subject to atmospheric air back diffusion into it. Air back diffusion will be less if the inside diameter of the line is small and the length of the line is long. Typically a tube having an outer diameter of 1/16" and an internal diameter of 0.030" will need 20 sccm of gas flowing out of it to prevent atmospheric air back diffusion. So, to be safe, one can choose the double i.e. 40 sccm. This new flow through the outlet back pressure regulator 44 leads to an extra 40 sccm. This results to a total preliminary flow from the selected channel 12, which is channel one, be equal to 75 sccm+40 sccm, i.e. 115 sccm.

Still with reference to FIG. 3, the unselected channel is back purged with the fluid sample coming from the selected channel. At all time, there is some flow in the derivation line 24 to prevent any inboard contamination and again to eliminate the effect of dead volume caused by this connecting point. The back purge flow of this unselected channel will be defined by second orifices 22, P-out and P2-N of the unselected channel. In fact, by adjusting P2-N, the back purge flow of the unselected channel may be adjusted as required. This back purge flow may be increased when the user has just switched channels to provide faster purging. This back purge flow may then be reduced to a convenient value just to provide enough flow to eliminate the undesirable effect of dead volume and to avoid air back diffusion.

From the above, one knows that the second orifice 22 of the selected channel must have a flow of 115 sccm plus some extra to purge the unselected channels. The forward flow through orifice 22 of the selected channel is fixed by P2-1 and P-out. One may set the inlet sample pressure value as needed since, in the field process, pressure is generally high and has to be reduced by an adjustable sample point pressure regulator. The sampling line pressure must be set just high enough to provide various flows to the fluid sampling system 10. This allows a higher velocity through the sampling line 14, thereby increasing speed of response to process change and reducing adsorption effect. So one can set intuitively or arbitrarily the P2-1 pressure at 75 Kpag as starting point. This gives a pressure differential of 40 Kpa on orifice 22 of the selected channel. Back purge flow through it may be easily determined by simply looking at FIG. 7, as will be described thereinafter.

Figure 6:
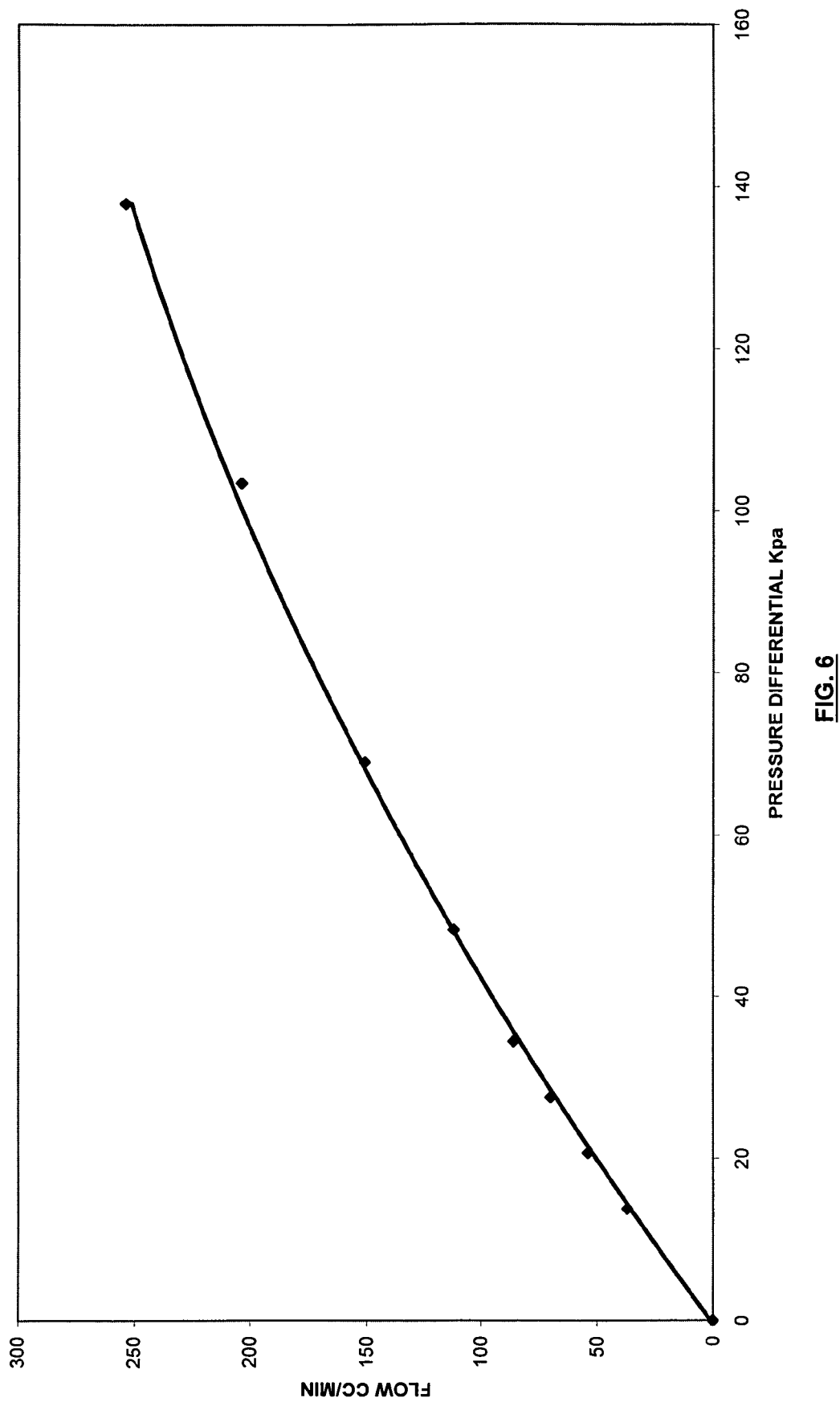
FIG. 6 is a diagram of flow versus pressure differential, in relation to the fluid sampling system of FIG. 3.
Figure 7:
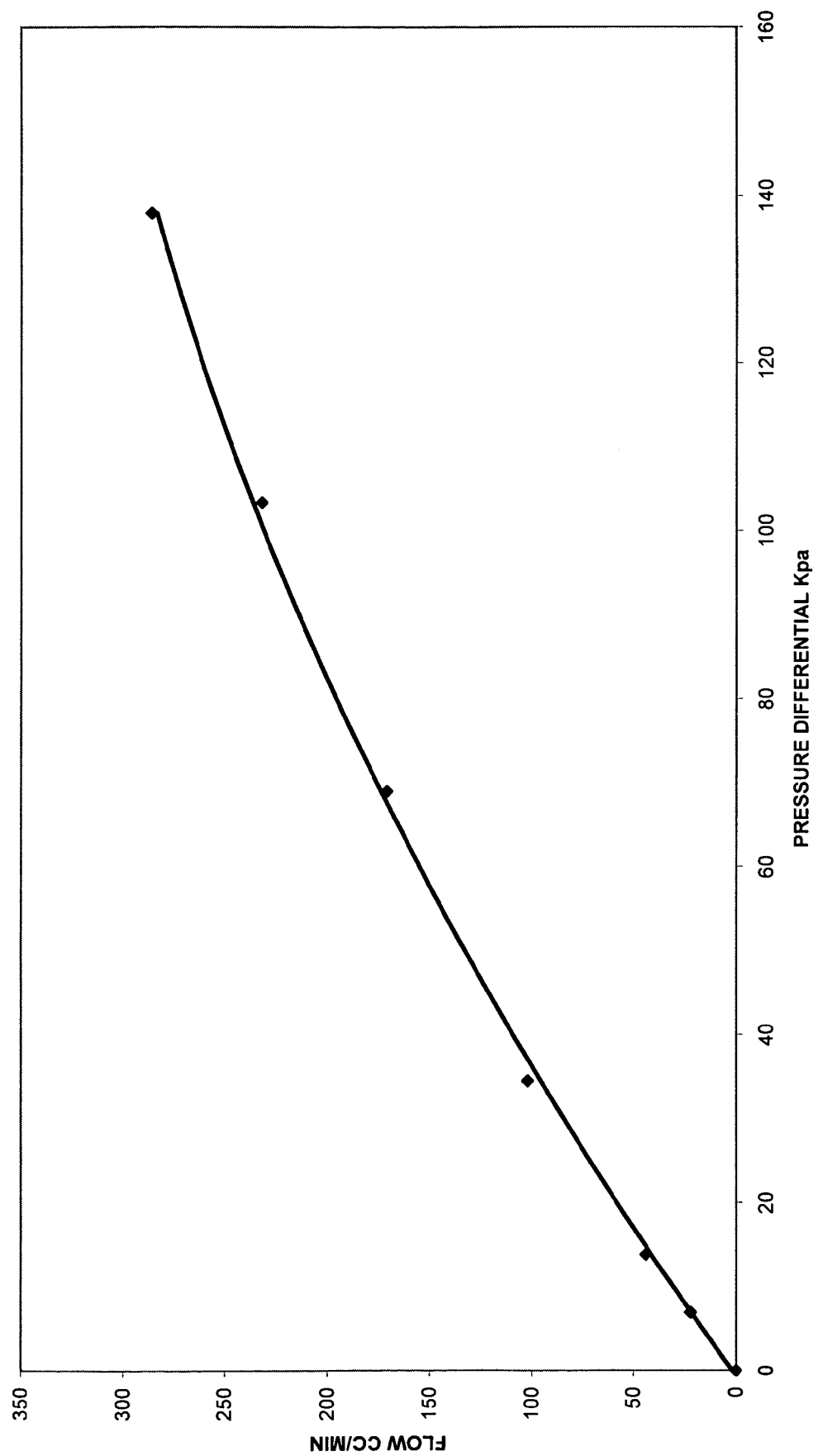
FIG. 7 is another diagram of flow versus pressure differential, in relation to the fluid sampling system of FIG. 3.

From these data's, orifice 22 of the selected channel is tuned to have a flow of 115 sccm at a pressure differential of 40 Kpa with inlet set at 75 Kpag and outlet set at 35 Kpag. When the orifice 22 of the selected channel is tuned, one performs flow measurement at various pressure differential to generate a flow curve. This curve is shown in FIG. 7. This is the flow characteristic for orifices 22. In FIG. 6, measurements are done with a back pressure equal to atmospheric pressure while in FIG. 7, measurements are done with 35 Kpag back pressure, the required pressure for the analytical system 30.

Now, in order to have a back purge flow through orifice 22 of the unselected channel, the P2-2 pressure must be lower than P-out. By looking at the curve illustrated in FIG. 7, one can see that a pressure differential on orifice 22 of the unselected channel of about 15 Kpag results in a flow of 45 sccm/min. This is more than enough to eliminate the effect of dead volume. So, for the unselected channel two, the back pressure regulator PC-2 is set to have a pressure of 20 Kpag at P2-2.

Now this leads to a total final forward flow through orifice 22 of the selected channel being equal to 75+40+45, i.e. 160 cc/min. From FIG. 7, 160 cc/min is obtained with a pressure differential of 70 Kpa. So this means that PC-1 backpressure regulator will have to be set at 105 Kpag.

The following steps are devoted to selections of orifices 20. So, we know that we must keep some flow through the derivation line 24 and back pressure regulator PC-1. This flow will be supplied by the corresponding orifice 20.

By setting inlet pressure to 170 Kpag and P2-1 at 105 Kpag, one settled the flow into the derivation line to simply avoid atmospheric air back diffusion to avoid contaminating the sample. As mentioned before the sytem is built with a 1/16"O.D. tubing having an internal diameter of 0.030". So a vent of 50 cc/min is a very safe value and allows some room for adjustment, as well known by a person versed in the art.

Figure 8:
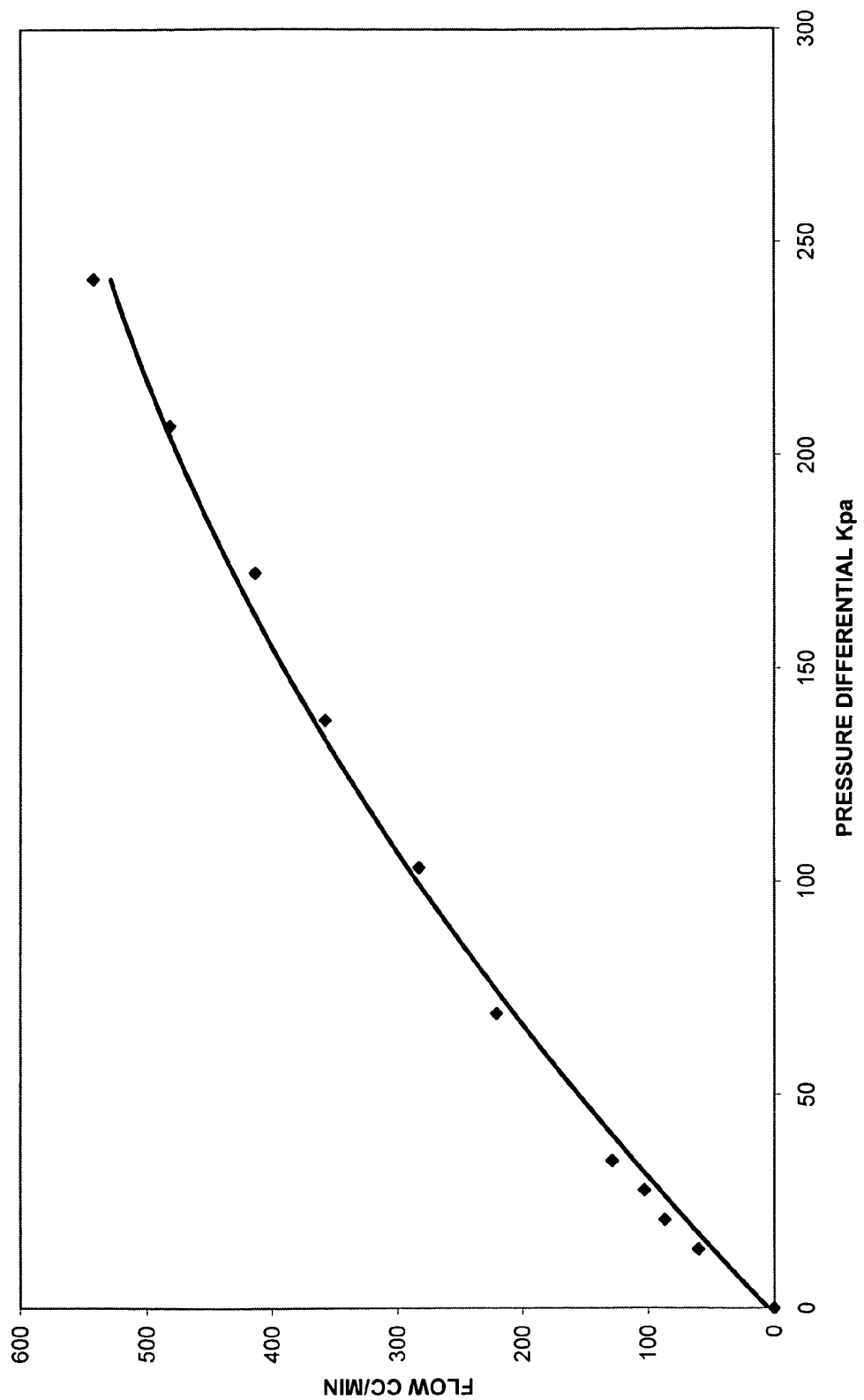
FIG. 8 is another diagram of flow versus pressure differential, in relation to the fluid sampling system of FIG. 3.
Figure 9:
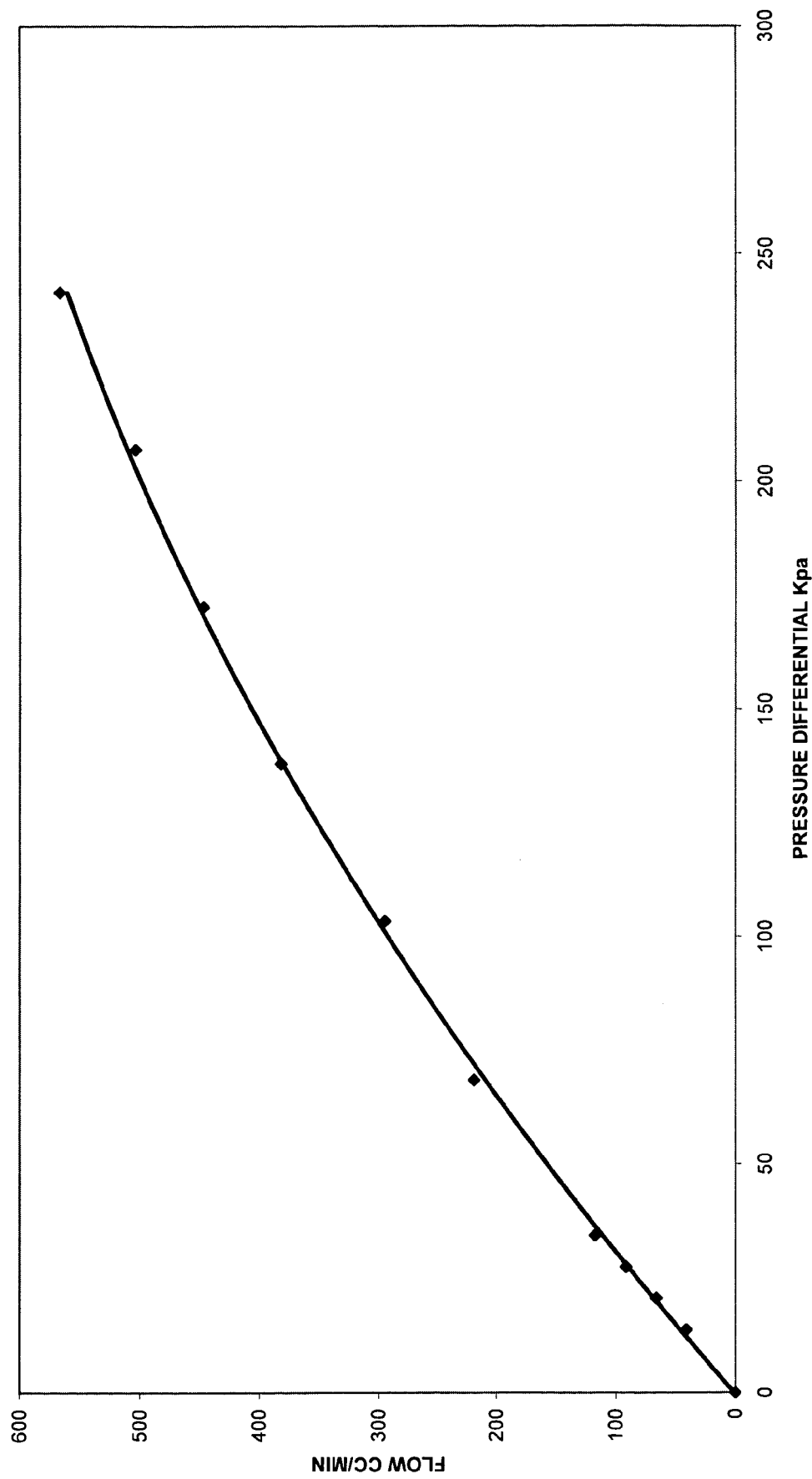
FIG. 9 is another diagram of flow versus pressure differential, in relation to the fluid sampling system of FIG. 3.

This leads that orifices 20 each must have a flow of 160 cc/min+50 cc/min at a pressure differential 65 Kpa, i.e. 170 Kpag-105 Kpag. So, these orifices 20 are tuned for these parameters and their flow curve done at many points. This gives the curve shown in FIG. 9. The flow through orifice 20 of the unselected channel is shown from the curve illustrated in FIG. 8. This is the flow curve of the orifice 20 done with a back pressure of 20 Kpag and a pressure differential of 150 Kpa i.e. inlet pressure of 170 Kpag less 20 Kpag.

Now, if one has to design a system with more sampling channels 12, one may adjust the system inlet pressure to allow enough gas flow to the unselected channel or readjust P2-N, or simply re-size the orifices 22. This is more a rule of thumb, than a strict mathematical relationship and this is well known in the art. The idea is to have enough flow in all parts of the system to eliminate the effect of any dead volume and prevent air back diffusion. Furthermore, if one allows more flow through PC-3, it automatically allows room for variation in back purge flow of unselected channels. For example, one may want to add one or more sampling channels to an existing system wherein orifices 20, 22 have already been sized. The flow through PC-3 can then be modified in acting on PC-3 while substantially keeping the output pressure constant for a convenient working of the analytical system 30.

Each system can be tuned for a particular application to take into account the molecular weight of the gas. If a system is tuned for Argon and H₂ is used instead, the volumetric flow of all vents and back purge will be higher. Pressure may be reduced to reduce total volumetric flow or maintained at same point if gas supply is not an issue.

Figure 5:
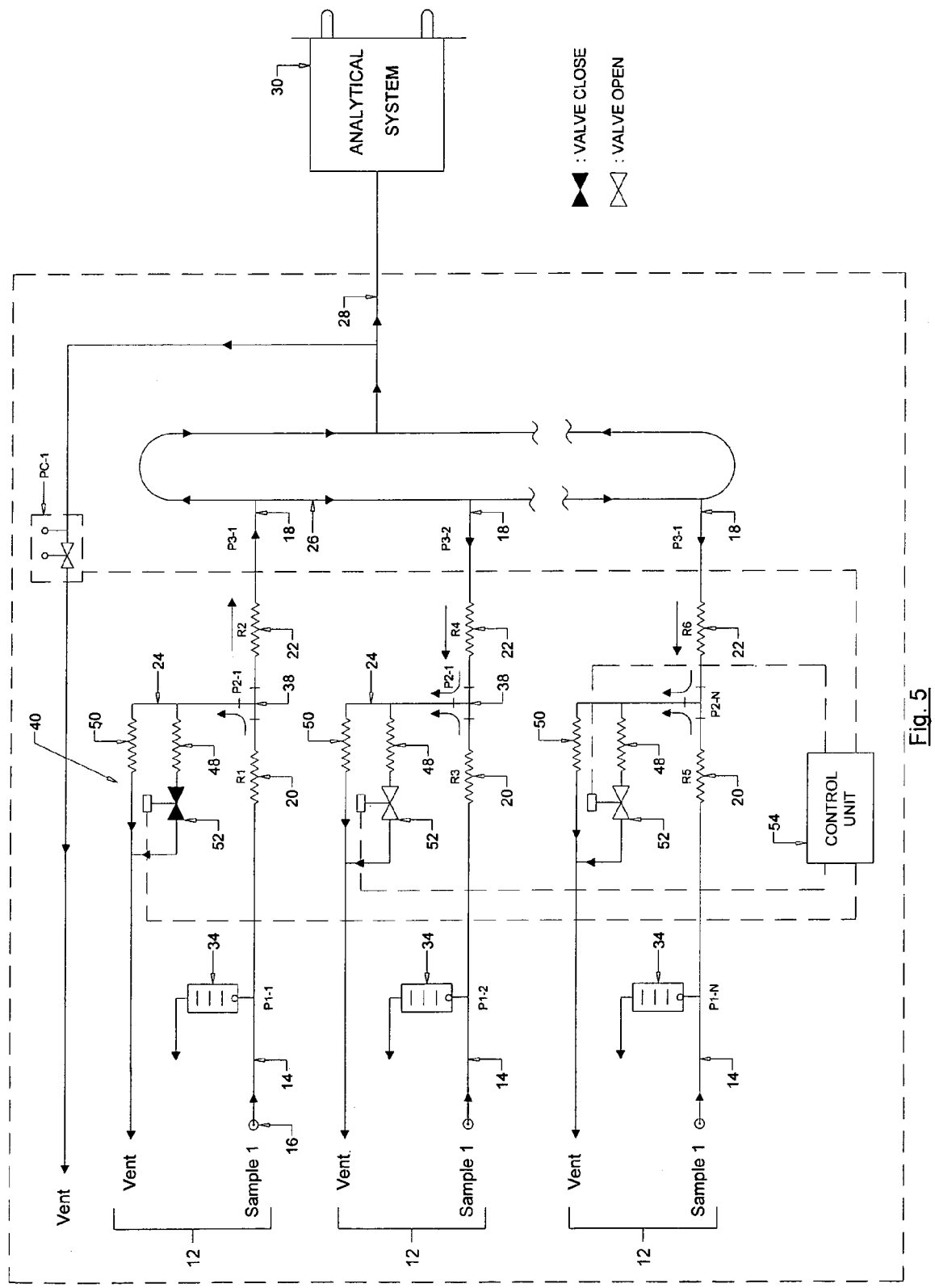
FIG. 5 is a schematic representation of a fluid sampling system according to another preferred embodiment of the present invention.

Referring now to FIG. 5, there is shown another preferred embodiment of the fluid sampling system 10 of the present invention. In this configuration, the pressure controllers PC-1, PC-2, PC-N have been replaced by a combination of a first calibrated derivation orifice 48 connected in series with an on-off valve 52 and these two elements are connected in parallel with a second calibrated orifice 50. When the on-off valve for channel one is closed, there is no flow through orifice 48, only in orifice 50. Orifice 50 is tuned to have a flow of 50 cc/min at 105 Kpag like derivation line flow of sampling channel one in FIG. 3. All other channels have their on-off valves opened. So their flow in their derivation line 24 is the sum of the flow through their orifices 48 and 50. Both orifices 48 and 50 are tuned to have a flow of 436 cc/min at 20 Kpag. This is the same derivation line flow of the unselected channel two of FIG. 3. So all channels having their on-off valves opened have P2 pressure less than P3. In this condition, their orifices 22 are back-purged and their inlet process fluid is vented through the derivation line 24. The channel having its on-off valve closed has P2 pressure higher than P3. So, its process fluid is forced s through the connecting line 26 and to the analytical system 30.

According to another aspect of the present invention and with reference to FIGS. 2 to 5, there is also provided a fluid sampling method preventing cross-port flow contamination between various sampling lines and not contaminating the sample by the product that is gassed out or adsorbed by the control means used to control flows of process fluids. Such a method can be used to sample a liquid or a gas. Accordingly, the method comprises the steps of:

a) providing a plurality of sampling channels 12, each of the sampling channels 12 comprising a sampling line 14 having an inlet 16, a regulated outlet 18, and first and second calibrated flow orifices 20, 22 connected in series between the inlet 16 and outlet 18;

b) connecting together the outlets 18 of the sampling lines 14 to provide a main regulated outlet 28;

c) providing fluids to the inlets 16 of the sampling lines 14;

d) deviating in a regulated manner the fluids from points located between the first and second flow orifices 20, 22 of the sampling lines 14; and e) after the steps a), b), c) and d), increasing pressure between first and second orifices 20, 22 of one of the sampling lines 14 which is then selected to provide a fluid sample at the main outlet 28, and decreasing pressure between first and second orifices 20, 22 of remaining sampling lines 14 to back purge the remaining sampling lines 14.

Preferably, the step a) comprises a step of calibrating the orifices 20, 22. More preferably, the step of calibrating further comprises a step of generating a calibration curve for each of the orifices 20, 22, as explained therein above. Also, preferably, in the step e), the increasing and decreasing of pressures is performed according to the calibration curves.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A fluid sampling system comprising:
    a plurality of sampling channels, each of said sampling channels comprising:
        a sampling line having an inlet, a regulated outlet, and first and second calibrated flow orifices connected in series between the inlet and outlet; and
        a controllable derivation line connected between the first and second orifices, for deviating fluid from the sampling line;
    a connecting line for connecting together the outlets of the sampling lines, the connecting line having a main regulated outlet for providing a fluid sample; and
    control means for controlling pressures between first and second orifices of all of the sampling lines by means of the controllable derivation lines, thereby increasing pressure between first and second orifices of one of the sampling lines which is then selected to provide said fluid sample to the outlet of the connecting line, and decreasing pressure between first and second orifices of remaining sampling lines to back purge said remaining sampling lines.

2. The fluid sampling system according to claim 1, comprising regulating means for regulating the inlets of said sampling lines.

3. The fluid sampling system according to claim 2, wherein said regulating means comprise a plurality of purge lines respectively connected between the inlet and the first orifice of each of the sampling lines.

4. The fluid sampling system according to claim 3, wherein each of said purge lines is provided with a purge flow controller connected to a vent line.

5. The fluid sampling system according to claim 1, wherein each of said sampling lines comprises a T-type of joint for connecting the corresponding controllable derivation line between the corresponding first and second orifices.

6. The fluid sampling system according to claim 1, wherein said control means comprise a plurality of pressure regulators respectively connected to the derivation lines for regulating pressure therein, thereby controlling said pressures between first and second orifices of the sampling lines.

7. The fluid sampling system according to claim 6, wherein said control means further comprise an outlet pressure regulator connected to the main outlet of the connecting line for regulating pressure therein, thereby controlling an output pressure at the main outlet.

8. The fluid sampling system according to claim 7, wherein said control means further comprise a control unit operatively connected to the outlet pressure regulator and to each of said pressure regulators for controlling said output pressure at the main outlet and said pressures between first and second orifices of all of the sampling lines.

9. The fluid sampling system according to claim 7, wherein the outlet pressure regulator and each of the pressure regulators comprises a back pressure regulator having a discharge side connected to a vent line.

10. The fluid sampling system according to claim 6, wherein each of said pressure regulators comprises a first and a second calibrated derivation orifice connected in parallel and an on-off valve connected in series with the first calibrated derivation orifice.

11. The fluid sampling system according to claim 1, wherein said connecting line is loop-shaped and connected between the main outlet and the outlets of the sampling lines.

12. A fluid sampling method comprising the steps of:
a) providing a plurality of sampling channels, each of said sampling channels comprising a sampling line having an inlet, a regulated outlet, and first and second calibrated flow orifices connected in series between the inlet and outlet;
b) connecting together the outlets of the sampling lines to provide a main regulated outlet;
c) providing fluids to the inlets of the sampling lines;
d) deviating in a regulated manner said fluids from points located between the first and second flow orifices of the sampling lines; and
e) after the steps a), b), c) and d), increasing pressure between first and second orifices of one of the sampling lines which is then selected to provide a fluid sample at the main outlet, and decreasing pressure between first and second orifices of remaining sampling lines to back purge said remaining sampling lines.

13. The fluid sampling method according to claim 12, wherein in said step c), the fluids are liquids.

14. The fluid sampling method according to claim 12, wherein in said step c), the fluids are gasses.

15. The fluid sampling method according to claim 12, wherein step a) comprises a step of calibrating said orifices.

16. The fluid sampling method according to claim 15, wherein said step of calibrating comprises a step of generating a calibration curve for each of said orifices.

17. The fluid sampling method according to claim 16, wherein, in said step e), the increasing and decreasing of pressures is performed according to the calibration curves.

* * * * *